United States Patent
Visvikis et al.

(10) Patent No.: US 12,220,220 B2
(45) Date of Patent: Feb. 11, 2025

(54) BODY SURFACE OPTICAL IMAGING FOR RESPIRATORY MONITORING

(71) Applicants: CENTRE HOSPITALIER RÉGIONAL ET UNIVERSITAIRE DE BREST, Brest (FR); UNIVERSITÉ DE BRETAGNE OCCIDENTALE, Brest (FR)

(72) Inventors: Dimitris Visvikis, Brest (FR); Erwan L'Her, Brest (FR); Souha Nazir, Brest (FR)

(73) Assignees: CENTRE HOSPITALIER RÉGIONAL ET UNIVERSITAIRE DE BREST, Brest (FR); UNIVERSITÉ DE BRETAGNE OCCIDENTALE, Brest (FR)

( * ) Notice: Subject to any disclaimer, the term of this patent is extended or adjusted under 35 U.S.C. 154(b) by 240 days.

(21) Appl. No.: 17/772,294

(22) PCT Filed: Sep. 18, 2020

(86) PCT No.: PCT/EP2020/076116
§ 371 (c)(1),
(2) Date: Apr. 27, 2022

(87) PCT Pub. No.: WO2021/083577
PCT Pub. Date: May 6, 2021

(65) Prior Publication Data
US 2022/0378320 A1   Dec. 1, 2022

(30) Foreign Application Priority Data
Oct. 31, 2019   (EP) ..................................... 19306417

(51) Int. Cl.
*A61B 5/08*   (2006.01)
*A61B 5/00*   (2006.01)
(Continued)

(52) U.S. Cl.
CPC .......... *A61B 5/0803* (2013.01); *A61B 5/0077* (2013.01); *A61B 5/0816* (2013.01);
(Continued)

(58) Field of Classification Search
CPC ..... A61B 5/0064; A61B 5/0077; A61B 5/091; A61B 5/1135; G01S 17/894
See application file for complete search history.

(56) References Cited

U.S. PATENT DOCUMENTS

| 10,342,464 B2 | 7/2019 | Niemeyer |
| 2010/0277571 A1 * | 11/2010 | Xu .......................... G06T 17/00 348/47 |

(Continued)

FOREIGN PATENT DOCUMENTS

| EP | 3245943 A1 * | 11/2017 |
| WO | 2010073129 A1 | 7/2010 |

OTHER PUBLICATIONS

T. Wentz et al, "Accuracy of dynamic patient surface monitoring using a time-of-flight camera and B-spline modeling for respiratory motion characterization", Physics in Medicine and Biology, vol. 57, pp. 4175-4193, 2012 (Year: 2012).*

(Continued)

*Primary Examiner* — Joel Lamprecht
*Assistant Examiner* — Nyrobi Celestine
(74) *Attorney, Agent, or Firm* — Maier & Maier, PLLC

(57) ABSTRACT

A method for measuring respiratory parameters of a subject using a range imaging sensor, wherein the method includes: receiving from the range imaging sensor at least one raw image of at least one portion of the torso of the subject, wherein each point of the raw image represents the distance between the range imaging sensor and the subject; generating a surface image of at least one portion of a surface of the torso of the subject by surface interpolation of the raw
(Continued)

image; estimating a respiratory signal as a function of time calculated as the spatial average, in a given region of interest (ROI) defined on the torso of the subject, of the differences between the depth values of the surface image at a given time and the depth values of a reference surface image; and estimating a lung volume.

16 Claims, 13 Drawing Sheets

(51) Int. Cl.
| | |
|---|---|
| A61B 5/091 | (2006.01) |
| A61B 5/11 | (2006.01) |
| A61B 5/113 | (2006.01) |
| G01S 17/894 | (2020.01) |
| G06T 3/60 | (2024.01) |
| G06T 7/33 | (2017.01) |
| G06T 7/80 | (2017.01) |

(52) U.S. Cl.
CPC ............ *A61B 5/091* (2013.01); *A61B 5/1128* (2013.01); *A61B 5/1135* (2013.01); *A61B 5/7203* (2013.01); *A61B 5/7278* (2013.01); *G01S 17/894* (2020.01); *G06T 3/60* (2013.01); *G06T 7/33* (2017.01); *G06T 7/80* (2017.01); *A61B 2560/0223* (2013.01)

(56) References Cited

U.S. PATENT DOCUMENTS

| | | | |
|---|---|---|---|
| 2011/0060215 | A1 | 3/2011 | Tupin, Jr. et al. |
| 2015/0265187 | A1 | 9/2015 | Bernal et al. |
| 2016/0345867 | A1 | 12/2016 | Aoki et al. |
| 2017/0055877 | A1* | 3/2017 | Niemeyer ............ A61B 5/0077 |
| 2020/0000370 | A1* | 1/2020 | Tao ........................ A61B 5/004 |
| 2020/0138336 | A1* | 5/2020 | Shim ..................... A61B 5/1135 |
| 2020/0187827 | A1* | 6/2020 | Addison ................. G06T 7/254 |

OTHER PUBLICATIONS

C. Sun et al, "An Unobtrusive and Non-Contact Method for Respiratory Measurement With Respiratory Region Detecting Algorithm Based on Depth Images", IEEE Access, vol. 7, pp. 8300-8315, Jan. 2019 (Year: 2019).*

International Search Report issued on Apr. 11, 2020 in corresponding International application No. PCT/EP2020/076116; 3 pages.

* cited by examiner (a)

(b)

(a)

(b)

(a)

(b)

(a)

(b)

(a)

(b)

BODY SURFACE OPTICAL IMAGING FOR RESPIRATORY MONITORING

FIELD

The present invention relates to the field of monitoring of physiological parameters. In particular, the present invention relates to the field of monitoring respiratory parameters of a patient by means of image analysis.

BACKGROUND

Mechanical ventilation, or assisted ventilation uses mechanical means to assist or replace spontaneous breathing. The clinical objectives of mechanical ventilation are to maintain gas exchange, reduce or replace respiratory effort, and monitor systemic $O_2$ consumption. Mechanical ventilation is implemented via devices called ventilators. These are artificial organs delivering air to the patient through a non-invasive device (via a mask or a nasal branch) or invasive (via the insertion of the tube). Constant monitoring of mechanically ventilated patients' respiratory parameters is essential to assess changes in airway dynamics but is currently only provided by invasive and airtight mask ventilation devices and not by non-airtight non-invasive ventilation devices (e.g. high-flow oxygen therapy systems). Mechanical ventilation is essential for the survival of patients suffering from respiratory failure. The ventilator delivers respiratory assistance either in pressure or in volume. During pressure ventilation, inspiratory pressure is adjusted by monitoring changes in volume caused by pressure changes that are not limited by the ventilator. An alarm on spirometry and tidal volume is set to avoid the risk of trauma. Volume ventilation requires adjustment of tidal volume or spirometry. It has been shown that setting parameters for mechanical ventilation is crucial especially for patients with unstable breathing and notably that anomalies in the tidal volume may cause damages like pulmonary lesions. For unstable patients, intubation is associated with a higher risk of complications.

In this context, continuous monitoring of the lung volumes allows clinicians to follow the state of health of these patients and improve their prognostics by taking actions, notably by fine tuning of ventilation parameters, which may advantageously result in reducing the risk of intubation, reducing the time of invasive ventilation and the risk of developing supplementary pulmonary lesions that may be caused by mechanical ventilation. Consequently, non-invasive, non-contact monitoring to continuously measure the respiration of patients on mechanical ventilation is a crucial service in clinical intensive.

Several clinical apparatuses are actually available for the monitoring of patient's ventilation. Most commonly used clinical apparatuses are respirators allowing both to replace the respiratory muscle by delivering air and the monitoring of ventilation parameters in order to adapt these parameters to the needs of the patient.

Nowadays in the clinical domain, there are no available non-invasive and contact-less monitoring system able to continuously monitor patient's ventilation. Techniques providing accurate respiratory measurements, such as plethysmograph, thoracic impedance, impedance pneumography, photo-plethysmograph and magnetometers are non-invasive. However, these techniques are cumbersome, expensive and not all adapted to the clinical environment.

Traditional techniques such as spirometer and pneumotachograph measure the rate of air flow during respiration. These contact techniques implement procedures depending from the cooperation of the patients. They allow to measure the lung volume, but they do not allow to detect anomalies on the movement of the thoracic cage, linked to pathologies such as pulmonary edema and thoracic regional dysfunction. The respiratory band is another well know contact non-invasive technique which allows to measure the respiratory rhythm of a patient.

Conventional respiratory detection is actually done with contact method that are considered disadvantageous for the patient and having a low accuracy. Indeed, in the field of analysis of respiratory dynamics, it is advantageous that no physical contact is established between the measurements system and the patient.

In this context the present invention intends to remedy to those drawbacks by proposing a method and a system for measuring respiratory parameters of a patient by non-invasive and contactless monitoring of patient's respiration.

Yet another domain of application for respiratory monitoring concerns the pulmonary function test, wherein the function of respiratory gas exchange is examined Some subject such as children, elderly people or subjects suffering from pulmonary disease such as chronic obstructive pulmonary disease may encounter some difficulties to perform this test using the spirometer due to the restraint sensation, because the mouthpiece and the nasal plug must be attached to the face of the subject under test or the lack of strength to perform forced expirations/inhalations. Moreover, measurement may be inaccurate due to occasional leaks of air-flow. Finally, the mouthpiece has to be changed for each patient.

In this context, the present invention offers a solution to those drawbacks by proposing a method and a system for measuring respiratory parameters of a patient in a non-invasive and contactless way.

SUMMARY

The present invention relates to a computer-implemented method for estimating respiratory parameters of a subject, wherein the method comprises:
  receiving a set of acquisitions derived from a range imaging sensor comprising at least one raw image of at least one portion of a torso of the subject, wherein each point of the raw image represents the distance between the range imaging sensor and the subject;
  generating a surface image of at least one portion of a surface of the torso of the subject by surface interpolation of the raw image;
  estimating a respiratory signal as a function of time calculated as the spatial average, in a given region of interest defined on the torso of the subject, of the differences between the depth values of the surface image at a given time and the depth values of a reference surface image, obtained from the set of acquisitions;
  estimating respiratory parameters including at least a lung volume as a function of time by multiplying the respiratory signal by the surface of the region of interest, and
  providing as output said respiratory parameters.

The present method is based on the analysis of 3D surface images (i.e. 3D point cloud) in order to estimate a unidimensional respiratory signal and further calculate other respiratory parameters.

Advantageously, this method provides an absolute quantitative estimation of respiration and the respiratory parameters of the subject in a real time and in a continuous way.

Advantageously, the present method allows accurate estimation of the respiratory parameters using raw data acquired with only one camera. Therefore, less data has to be analyzed in order to estimate the respiratory parameters which allows to reduce the computation time and contribute to the real time implementation of the method.

The respiratory parameters according to the definition of the present invention are also known as respiratory volumes. Lung capacities are derived from a summation of different respiratory volumes and represent the amount of air that can be inhaled or exhaled during one respiratory cycle. In the present invention, the thoracic region motion (chest wall motion) may be tracked by the analysis of the 3D spatial information provided by the range imaging sensor. The difference between the surface image (chest wall shapes) with respect to a reference surface image provides an information about the amount of air that can be inhaled or exhaled, allowing to accurately estimate lung volume (variation of the chest wall with respect to a reference).

In one embodiment, the present invention relates to a method for measuring respiratory parameters of the subject using a range imaging sensor, wherein the method comprises:
- receiving from the range imaging sensor at least one raw image of at least one portion of the torso of the subject, wherein each point of the raw image represents the distance between the range imaging sensor and the subject;
- generating a surface image of at least one portion of a surface of the torso of the subject by surface interpolation of the raw image;
- estimating a respiratory signal as a function of time calculated as the spatial average, in a given region of interest (ROI) defined on the torso of the subject, of the differences between the depth values of the surface image at a given time and the depth values of a reference surface image;
- estimating a lung volume as a function of time by multiplying the respiratory signal by the surface of the region of interest.

In the present invention, the region of interest defined on the torso comprises the body region going from the shoulders to the hipbones of the subject. The thoracic respiration mainly depends on the contraction of the intercostal muscles, while the abdominal breathing mainly depends on diaphragmatic muscle contraction. Chest wall movements include both thoracic breathing and abdominal breathing. Hence, in the present invention, the breathing movements of the whole torso region are considered, advantageously allowing a more accurate estimation of the respiratory parameters.

According to one embodiment, the method of the present invention is a computer-implemented method.

The present method advantageously allows non-invasive and contact-less monitoring of respiratory parameters of a subject in real time. This monitoring provides clinicians with useful information allowing to improve the efficiency of mechanical ventilation of a patient by fine tuning of the ventilation parameters, notably by tuning the amount of air volume or pressure to deliver. The monitoring of the respiratory parameters therefore allows to reduce the time of mechanical ventilation, thus preventing the occurrence of supplementary lungs lesions caused by this ventilation. The monitoring of respiratory parameters also allows the detection of the presence of respiratory abnormalities such as pneumothorax, atelectasis, diaphragmatic paradox. The monitoring of respiratory parameters, especially in patient invasively ventilated for a long period of time, also allows to check, during or after suspension of invasive ventilation, their state of health.

According to one embodiment, the method further comprises estimating a tidal volume as the difference between the maximum value and the minimum value in one respiratory cycle of the respiratory signal multiplied by the surface of the region of interest.

According to one embodiment, the method further comprises estimating a respiratory rate calculated from the detection of inspiration peaks in the respiratory signal.

In one embodiment, the respiratory parameters include, in addition to the lung volume, the tidal volume, the minute volume, the respiratory rate, the vital capacity, expiratory reserve volume, inspiratory reserve volume, inspiratory capacity and/or inspiratory vital capacity. The inspiratory and expiratory reserve volume may only be estimated on awaken subject able to perform forced inspiration and expiration.

According to one embodiment, the surface image is obtained using basis spline functions.

According to one embodiment, the range imaging sensor is a time-of-flight (ToF) camera.

According to one embodiment, the method further comprises a step of filtering the raw image so as to remove noise originating from other objects in the scene.

According to one embodiment, the method further comprises a calibration step applying a rotation matrix to the raw image so as to align the subject torso in the raw image with the xy plane of the range imaging sensor.

The calibration advantageously allows to align the subject torso in the raw image with the xy plane of the range imaging sensor so that the method may be implemented for a subject no matter his/her actual position as long as is torso is comprised in the field of view of the camera. As consequence, the present method is adapted to estimate respiratory parameters for a subject standing, sitting or lying.

According to one embodiment, the method further comprises a step of controlling a ventilator by modifying the value of at least one ventilation parameter, wherein the value of said ventilation parameter is calculated using at least one of the estimated respiratory parameters, notably the tidal volume. This embodiment advantageously allows to decrease the occurrence of lesions caused by ventilation.

The present invention also relates to a program comprising instructions which, when the program is executed by a computer, cause the computer to carry out the steps of the method according to any one of the embodiments hereabove.

The present invention also relates to a non-transitory computer readable medium comprising instructions which, when the program is executed by a computer, cause the computer to carry out the steps of the method according to any one of the embodiments hereabove.

In what follows, the modules are to be understood as functional entities rather than material, physically distinct, components. They can consequently be embodied either as grouped together in a same tangible and concrete component, or distributed into several such components. Also, each of those modules is possibly itself shared between at least two physical components. In addition, the modules are implemented in hardware, software, firmware, or any mixed form thereof as well.

The present invention further relates to a system for measuring respiratory parameters of a subject comprising:
- an acquisition module configured to control a range imaging sensor for the acquisition of at least one raw image comprising at least one portion of the torso of the subject, wherein each point of the raw image represents the distance between the range imaging sensor and the subject;

a surface generation module configured to generate a surface image of at least one portion of the surface of the torso of the subject by surface interpolation of the raw image;

a calculation module configured to calculate a respiratory signal as a function of time as the spatial average, in a given region of interest defined on the torso of the subject, of the differences between the depth values of the surface image at a given time and the depth values of a reference surface image and to calculate a lung volume as a function of time by multiplying the respiratory signal by the surface of the region of interest.

The present invention also relates to a system for estimating respiratory parameters of a subject comprising:

an input module configured to receive a set of acquisitions derived from a range imaging sensor, said set of acquisitions comprising at least one raw image comprising at least one portion of a torso of the subject, wherein each point of the raw image represents the distance between the range imaging sensor and the subject;

a surface generation module configured to generate a surface image of at least one portion of a surface of the torso of the subject by surface interpolation of the raw image;

a calculation module configured to calculate a respiratory signal as a function of time as the spatial average, in a given region of interest defined on the torso of the subject, of the differences between the depth values of the surface image at a given time and the depth values of a reference surface image, obtained from the set of acquisitions, and to calculate respiratory parameters including at least a lung volume as a function of time by multiplying the respiratory signal by the surface of the region of interest;

an output module configured to output said respiratory parameters.

In one embodiment, the calculation module is configured to further calculate a respiratory rate calculated from the detection of inspiration peaks in the respiratory signal.

In one embodiment, the calculation module is further configured to calculate a tidal volume as the difference between the maximum value and the minimum value in one respiratory cycle of the respiratory signal multiplied by the surface of the region of interest According to one embodiment, the system further comprises a range imaging sensor and an acquisition module configured to control a range imaging sensor for the acquisition of the set of raw images.

According to one embodiment, the system further comprises a time-of-flight camera with infrared light illumination.

According to one embodiment, the range imaging sensor is placed in front of the torso of the subject.

According to one embodiment, the range imaging sensor is a time-of-flight camera and the system comprises a calibration module configured to apply a rotation matrix to the raw images so as to align the subject torso in the raw images with the xy plane of the time-of-flight camera.

According to one embodiment, the surface generation module is further configured to filter the raw image so as to remove noise originating from other objects in the scene.

In the present invention, the following terms have the following meanings:

"Lung volume" refers to the volume of air in the lungs at different phases of the respiratory cycle.

"Processor" this term is herein not restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

"Real time": refers to the ability of a system of controlling an environment by receiving data, processing them, and returning the results sufficiently quickly to affect the environment at that time. Real-time responses (i.e. output) are often understood to be in the order of milliseconds, and sometimes microseconds.

"Respiratory parameters" refers to the lung volume, the tidal volume and the minute volume calculated on a ROI comprising the whole torso of the patient or on multiple ROIs corresponding to the abdominal region, thorax region, left or right lung region. In addition the respiratory parameters further refers to the vital capacity (i.e. the volume of air breathed out after the deepest inhalation), expiratory reserve volume (i.e. the maximal volume of air that can be exhaled from the end-expiratory position), inspiratory reserve volume (i.e. the maximal volume that can be inhaled from the end-inspiratory level), inspiratory capacity (i.e. the sum of inspiratory reserve volume and tidal volume) and inspiratory vital capacity (i.e. the maximum volume of air inhaled from the point of maximum expiration). The inspiratory and expiratory reserve volume may only be estimated on awaken subject able to perform forced inspiration and expiration.

"Subject" refers to a mammal, preferably a human. In the sense of the present invention, a subject may be an individual having any mental or physical disorder requiring regular or frequent medication or may be a patient, i.e. a person receiving medical attention, undergoing or having underwent a medical treatment, or monitored for the development of a disease.

"Tidal volume" refers to the normal volume of air displaced between normal inhalation and exhalation when extra effort is not applied. This respiratory parameter is expressed in ml.

"Trunk" or "torso" refers to the central part or core of many animal bodies (including humans) from which extend the neck and limbs. The torso includes: the thoracic segment of the trunk (i.e. thorax or chest), the abdominal segment of the trunk (i.e. the abdomen, which is the part of the body between the thorax and pelvis) and the perineum.

BRIEF DESCRIPTION OF THE DRAWINGS

The following detailed description will be better understood when read in conjunction with the drawings. For the purpose of illustrating, the system and the block diagrams describing the method are shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Features and advantages of the invention will become apparent from the following description of embodiments of a system, this description being given merely by way of example and with reference to the appended drawings in which.

The comparison of the two methods using the Bland-Altman plot demonstrates low bias (7.90 ml) and deviation (<±22.03 ml).

Figure 9:
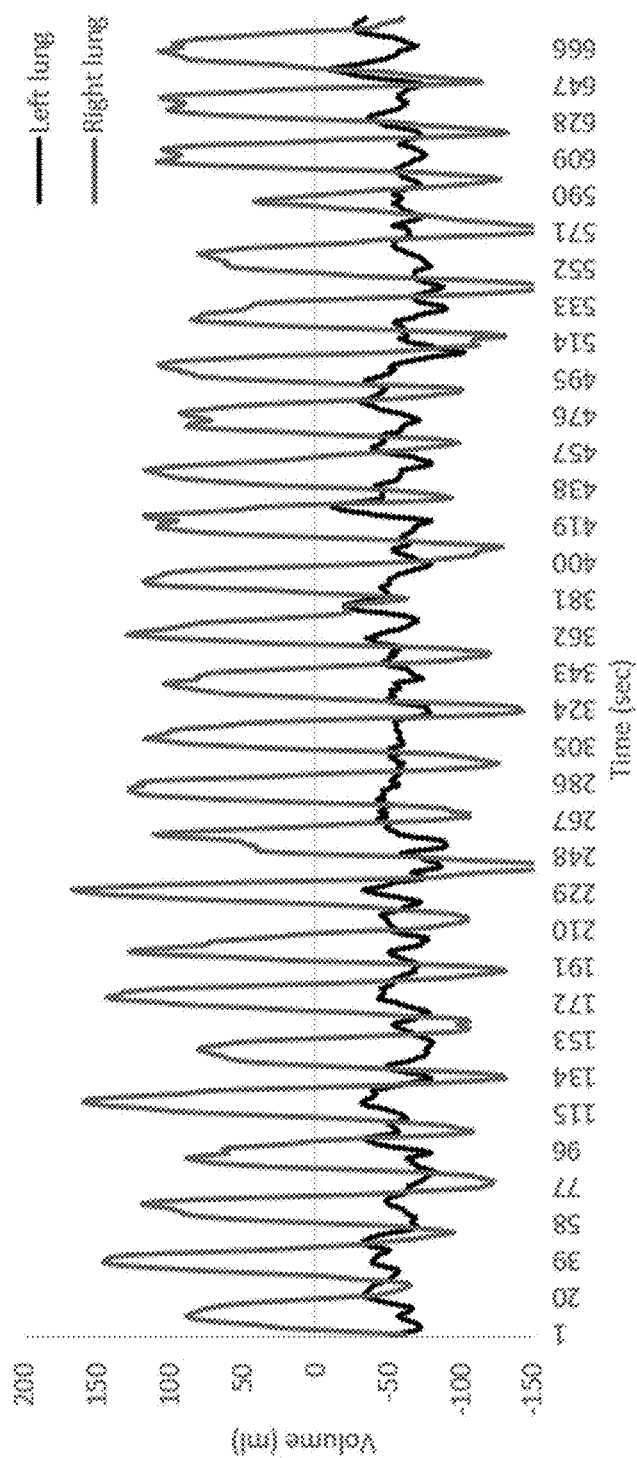

FIG. 9 is a plot representing regional ventilation estimation in the left and right parts of the mannequin's thorax. The volume time curve is obtained by analyzing the right and left lung ROIs separately using the mannequin's asynchrony mode of ventilation. The black curve corresponds to the volume time curve of the left thorax and the gray curve corresponds to the volume time curve of the right thorax.

Figure 10:
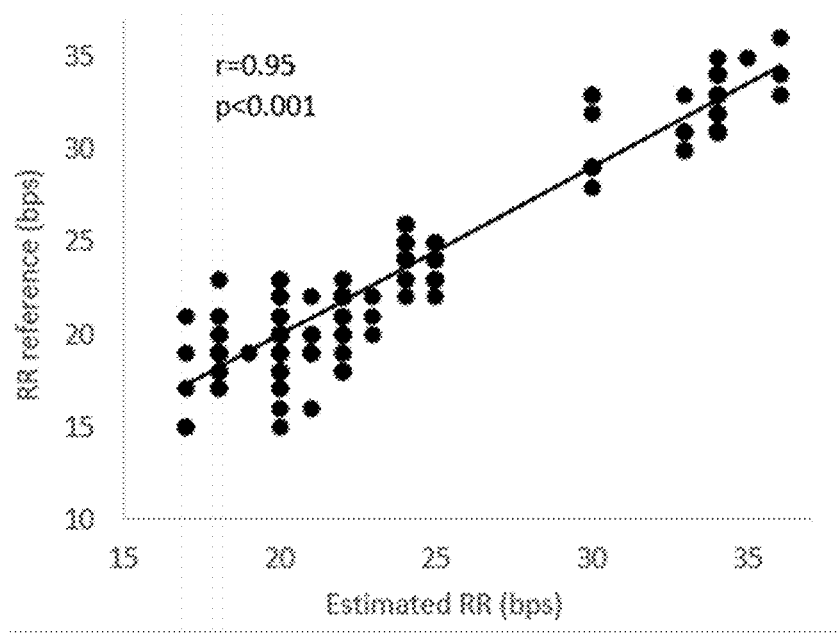
Figure 10:
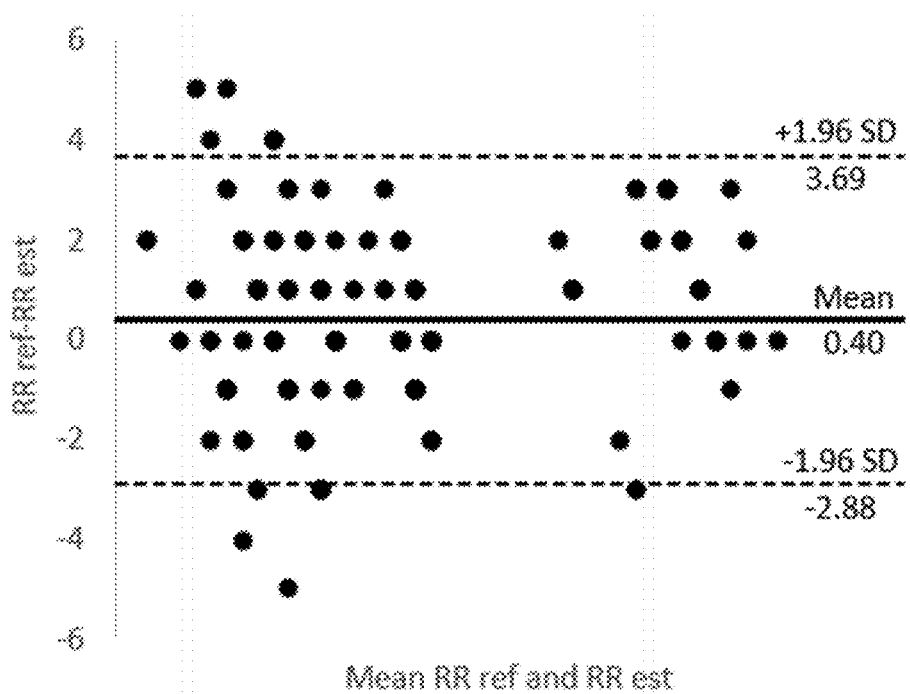

FIGS. 10(a) and (b) are a correlation and a Bland-Altman plot for reference and estimated respiratory rates. Reference RR values are provided by the ventilator for patients under ventilation assistance. Estimated RR was performed using the Kinect based monitoring system. On the 16 ICU patients' recordings, the estimation of the RR was highly correlated with the reference method (r=0.95; p<0.001). The comparison of the two methods using the Bland-Altman plot demonstrates low bias (0.40 bps) and deviation (<±1.67 bps).

FIGS. 11(a) and (b) are a correlation and Bland-Altman plot for reference and estimated tidal volume. Reference Vt values are provided by the ventilator for patients under ventilation assistance. Estimated Vt was performed using the kinect based monitoring system. On the 16 ICU patients' recordings, the estimation of the Vt correlated with the reference method (r=0.90; p<0.001). The comparison of the two methods using the Bland-Altman plot demonstrates low bias (−5.36 ml) and acceptable deviation (<±23.70 ml).

Figure 12:
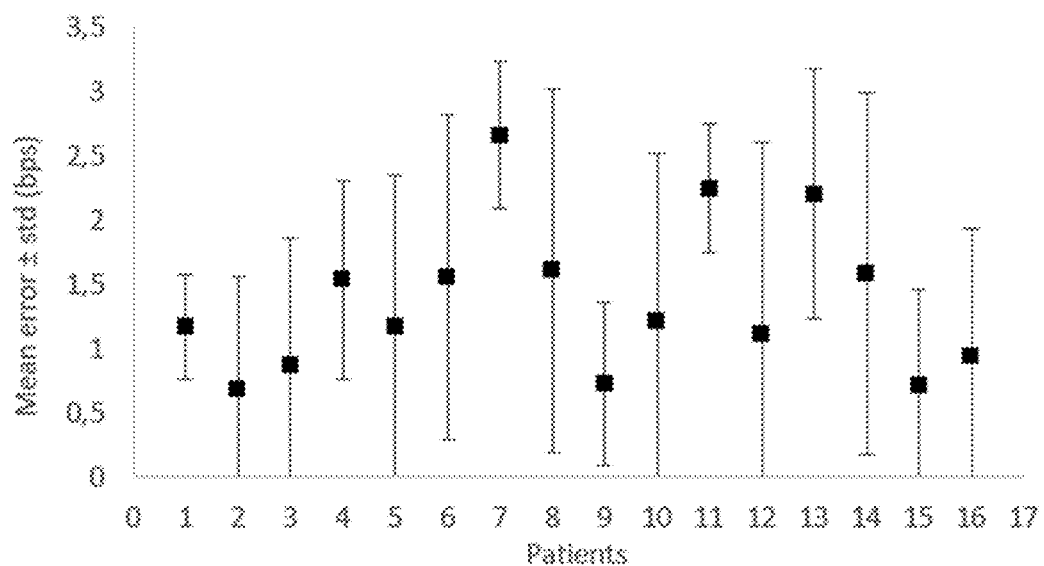

FIG. 12 is a plot representing patient's mean error more or less the standard deviation of the estimated RR.

Figure 13:
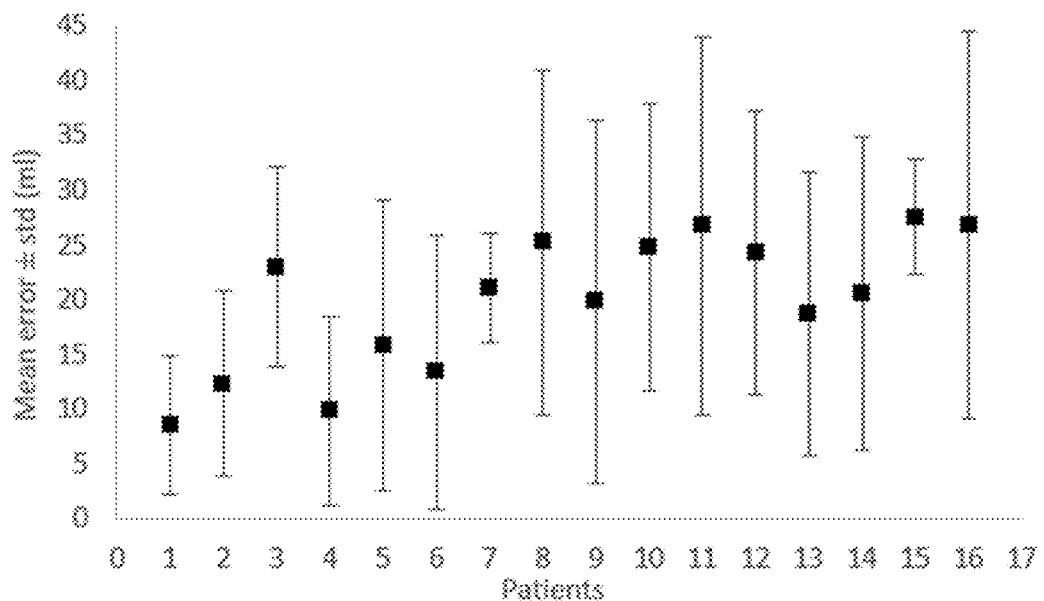

FIG. 13 is a plot representing patient's mean error more or less standard deviation of the estimated Vt.

FIG. 14(a) represents the equal, and (b) unequal ventilation in the left and right thorax of two ICU patients. The volume time curve is obtained by analyzing the right and left lung ROIs separately. The black curve corresponds to the volume time curve of the left thorax and the gray curve corresponds to the volume time curve of the right thorax.

FIG. 15(a) represents the synchronic, and (b) asynchronous ventilation between the thorax and abdomen of two ICU patients. The volume time curve is obtained by analyzing the thorax and abdomen ROIs separately. The black curve corresponds to the volume time curve of the abdomen and the gray curve corresponds to the volume time curve of the thorax.

While various embodiments have been described and illustrated, the detailed description is not to be construed as being limited hereto. Various modifications can be made to the embodiments by those skilled in the art without departing from the true spirit and scope of the disclosure as defined by the claims.

DETAILED DESCRIPTION

Figure 1:
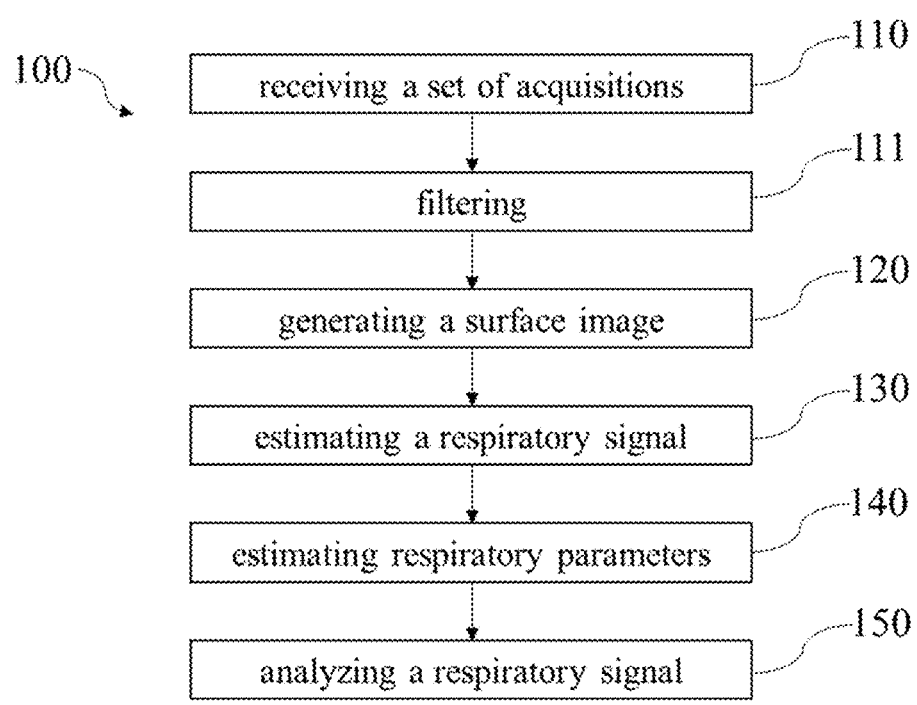
FIG. 1 is a block diagram representing the steps of the method according to one embodiment of the invention.

FIG. 1 shows a diagram block representing some of the main steps of the method 100 for measuring respiratory parameters of a subject using a range imaging sensor. In one preferred embodiment, the subject is a patient under mechanical ventilation.

Since the clinical environment in an Intensive Care Unit, Recovery Room, medical emergency services and the like, are equipped of multiple health care devices (i.e. monitor, ventilation device, cardiac monitoring device, etc.) and that all these equipment have to be displaced so as to allow easy and fast access to the patient for care administration or in case of emergency, the range imaging sensor may be advantageously placed on top of the patient bed.

In one embodiment, the first step of the method consists in receiving of at least one raw image of at least one portion of the torso of the patient acquired from a range imaging sensor 110. Each point of the raw image acquired from a range imaging sensor represents the distance between the range imaging sensor and the patient.

A variety of range imaging sensors or cameras are currently available which are based on different types of range imaging technics such as stereo triangulation, sheet of light triangulation, structured light, interferometry, coded aperture and any other technics known by the man skilled in the art.

According to one preferred embodiment, the range imaging sensor is a time-of-flight (ToF) camera. A ToF camera is a range imaging camera system that employs time-of-flight techniques to resolve distance between the camera and the subject for each point of the image, by measuring the round-trip time of an artificial light signal provided by a laser, laser diodes or a LED of different wavelengths, notably infrared or near infrared. Rather than measuring the intensity of the ambient light, as with standard cameras, ToF cameras measure the reflected light coming from the camera's own light-source emitter.

Different measurement principles of time-of-flight cameras may be used for the purpose of the present invention, including: (i) pulsed-light cameras, which measure directly the time taken for a light pulse to travel from the device to the object and back again, and (ii) continuous-wave modulated-light cameras, which measure the phase difference between the emitted and received signals, and hence obtain the travel time indirectly.

ToF cameras may combine a single or multiple laser beams, possibly mounted onto a rotating mechanism, with a 2D array of light detectors and time-to-digital converters, to produce 1-D or 2-D arrays of depth values.

The ToF camera, from which the raw images are received in the present method, may comprised two types of sensors: pulsed-light sensor or continuous-wave modulation sensor. Pulsed-light sensors directly measure the round-trip time of a light pulse. The width of the light pulse is of a few nanoseconds. Continuous-wave (CW) modulation sensors measure the phase differences between an emitted continuous sinusoidal light-wave signal and the backscattered signals received by each photodetector. The phase difference between emitted and received signals is estimated via cross-correlation (demodulation). The phase is directly related to distance, given the known modulation frequency. These sensors usually operate indoors, and are capable of short-distance measurements only (from a few centimeters to several meters) and therefore are advantageously adapted for use in a clinical environment.

ToF cameras allow rapid acquisition and rapid real-time processing of scene information. ToF cameras are characterized by a high acquisition frequency allowing a 3D analysis of a volume in real time. The surface information provided from this type of camera is advantageously adapted for the management and the monitoring of dynamic movements.

Contrary to radar systems, having a transmitting and receiving antenna, the use of a range imaging sensor is particularly advantageous. Indeed, the transmitting antenna uses electromagnetic waves that may have some second side effect on the patient and disrupt the functioning of other medical device inside (i.e. peacemakers or insulin pumps) or in proximity of the patient. Inversely the present method and system are configured to use infra-red radiations which does not cause secondary effects for the patient and do not produce perturbations in the functioning of medical devices in the clinical environment. Furthermore, images obtained from range imaging sensors allows to have granular information on the displacement of the whole torso of the patient while the use of radar system only provide punctual information resulting in a poorer estimation of the lung volume.

The method may be as well configured to provide instructions to a range imaging sensor in order to control the image acquisition and transfer to a data processing device configured to carry out the steps of the present method. The image acquisition may be planned on the base of a predefined time schedule or triggered when a triggering signal is received.

When using a ToF camera implementing continuous-wave modulation technology, the cross-correlation between the optical powers of the emitted signals s(t) and the optical powers of the received signal r(t), resulting from the reflection of the light on the imaged object, is expressed according to the following equation:

$$C(x) = \lim_{T \to \infty} \frac{1}{T} \int_{-T/2}^{+T/2} s(t) r(t-x) dt \qquad (1)$$

If considering the values of the correlation function at four equally spaced samples within one modulation period:

$$C\left(i \cdot \frac{\pi}{2}\right) i = 0, \ldots, 3$$

these four sample values are sufficient for the unambiguous computation of the phase φ obtained as follow:

$$\varphi = \arctan\left(\frac{C(\tau_0) - C(\tau_2)}{C(\tau_1) - C(\tau_3)}\right) \qquad (2)$$

A depth value d at each pixel is computed with the following formula:

$$d = \frac{c}{4\pi f} \varphi \qquad (3)$$

wherein c is the light speed and f is the modulation frequency.

According to one embodiment, the ToF camera comprises a transmitter, a light emitter (generally a LED, or light-emitting diode) configured to send light onto an object so that the time that the light needs to travel from the illumination source to the object and back to the sensor is measured. In the case of continuous-wave (CW), the emitted signal is a sinusoidal modulated light signal. The received signal is phase-shifted due to the round trip of the light signal. Moreover, the received signal is affected by the object's reflectivity, attenuation along the optical path and background illumination. Each pixel independently performs demodulation of the received signal and therefore is capable of measuring both its phase delay as well as amplitude and offset (background illumination).

The raw image is a depth map, or depth image that may be presented under the form of a bidimensional array representing a grey level image or an RGB image, wherein the size of the array depends on the ToF camera, notably the photosensor used for image acquisition. The raw image may be for example coded in 16 bits where the information on the depth measure in each pixel (u, v) correspond directly to the distance between the ToF camera and the object (i.e. the patient).

According to one embodiment, the method further comprises a calibration step consisting in the application of a rotation matrix to the raw image so as to align the patient torso in the raw image with the xy plane of the time-of-flight camera. In one example, the three following rotations:

$$R_x = \begin{bmatrix} 1 & 0 & 0 \\ 0 & \cos\alpha & -\sin\alpha \\ 0 & \sin\alpha & \cos\alpha \end{bmatrix} \qquad (4)$$

$$R_y = \begin{bmatrix} \cos\beta & 0 & \sin\beta \\ 0 & 1 & 0 \\ \sin\beta & 0 & \cos\beta \end{bmatrix} \quad (5)$$

$$R_y = \begin{bmatrix} \cos\gamma & -\sin\gamma & 0 \\ \sin\gamma & \cos\gamma & 0 \\ 0 & 0 & 1 \end{bmatrix} \quad (6)$$

are applied to the raw image according to the equation:

$$\begin{bmatrix} X_t \\ Y_t \\ Z_t \end{bmatrix} = R \times \begin{bmatrix} X_i \\ Y_i \\ Z_i \end{bmatrix} \quad (7)$$

wherein $(X_t, Y_t, Z_t)$ are the coordinates of the points transformed from the rotation matrix $R=R_x \times R_y \times R_z$, $\alpha$, $\beta$ and $\gamma$ are the angles in radians along the three axis of the ToF camera and $(X_i, Y_i, Z_i)$ are the coordinates of the points of the raw image acquired by the ToF camera.

According to one embodiment, the method further comprises a step of filtering the raw image so as to remove noise originating from other objects in the scene 111.

In one embodiment, the method comprises the step of generating a surface image of at least one portion of the surface of the torso of the patient by surface interpolation of the raw image 120. In one embodiment, the surface image is obtained using basis splines (also called B splines) functions on the raw image. B-spline function is a combination of flexible bands that passes through the number of points that are called control points and creates smooth curves. These functions enable the creation and management of complex shapes and surfaces using a finite number of points. B-spline function and Bézier functions are applied extensively in shape optimization methods. This embodiment advantageously allows to derive the respiratory motion dynamics on a point by point basis rather than a region by region basis. Furthermore, the B-spline modeling significantly improves the depth estimation accuracy and reduces the error on the respiratory signal measurement to 0.22±0.14 mm and it improves the measurements repeatability by a factor of 3.

In one embodiment, the method comprises a step 130 of obtaining the respiratory signal as a function of time by analyzing data in a given region of interest (ROI) defined on the torso of the patient. The respiratory signal as a function of time is then estimated as the spatial average in said given ROI of the differences between the depth values of the surface image at a given time and the depth values of a reference surface image. The reference surface image may be the first image of the set of acquisition. Advantageously, the use of this reference surface image allows to define the baseline drift. In fact, respiratory signals are relative to reference values, known as baselines. The baseline for a respiratory measurement is defined by the reference image (ideally the zero-flow line).

The respiratory signal as a function of time is therefore obtained as:

$$D(k) = \frac{1}{N} \sum_{k=0}^{N} (L_i - R_i) \quad (8)$$

wherein R represent the reference surface image, L represent the surface image of the torso corresponding to the k-th depth image acquired and N is the number of pixels in the region of interest defined on the torso of the patient.

Advantageously, the position of the reference plane (i.e. reference surface image) is not important in estimation of the tidal volume and does not affect the accuracy of volume difference between surfaces.

According to one embodiment, the region of interest is predefined manually by a user. According to an alternative embodiment, the position and dimensions of the region of interest are automatically defined on the torso of the patient by means of a deep learning algorithm. Said deep learning algorithm is configured to receive as input an RGB image of the patient, notably comprising at least the torso of the patient, and provide as output a model of the skeleton of the subject (i.e. spatial distribution of the bones and joints of the patient). A real time tracking of the skeleton model may be implemented based on a deep learning algorithm. The model of the skeleton of the subject is then used to select at least one region of interest. In one embodiment, one region of interest is defined as the region going from the hipbones to the shoulder gilders corresponding to the whole torso. In another embodiment, two regions of interest are defined on the torso: a thoracic region, comprising the ribs, the sternum and shoulder gilders, and an abdominal region comprised between the diaphragm and the hipbones. Alternatively, a first region may be defined on the left side of the rib cage so as to cover the left lung and a second region may be defined on the right side of the rib cage so as to cover the right lung.

In one example, the deep learning algorithm for real time tracking of the skeleton model is based on Deep Neural Net model to perform Human Pose Estimation. It has been shown that this algorithm is able to accurately predict the location of various human "key points" (joints and landmarks) such as elbows, knees, neck, shoulder, hips, chest etc. In one embodiment, the Deep Neural Net model is configured to take a color image of the patient as input, and to produce as output the 2D locations of "key points" (i.e. spatial distribution of the bones and joints of the patient). Each coordinate in the skeleton is known as a joint. A pre-trained model may be used on a dataset to detect human joints that produces 18 points including face and body "key points". The set of coordinates may be subsequently connected to identify a ROI. The patient torso ROI may be then defined by the surface connecting the identified joints of shoulders and hipbones. This ROI detection algorithm may as well be used to track the movement of the patient.

The lung volume as a function of time is obtained by calculating the volume of the ROI at each frame. This is done by calculating the difference between the current depth surface and reference depth surface for all pixels in the ROI. The size of ROI is then crucial to obtain the volume. The size of ROI may be measured as the number of pixels the ROI with dimensions in $mm^2$. Preferably, the size of the ROI is the area measured as the product of the width for the length of the ROI. The width and length are defined as the distance between the minimum and maximum coordinates of the pixels within the ROI along x and y axis respectively. Since an intrinsic camera calibration is performed before starting image acquisition to find the relation between camera's natural units (pixel positions in the image) and real-world units (in mm), it is possible to just multiply the surface dimension by the depth difference (between actual and reference surface).

Advantageously, using surfaces (3D cloud of point) for the estimation of the respiratory parameters (instead of 2D image) allows to avoid an additional step of calibration by means of a scaling factor depending from the intrinsic parameter of the camera, notably the camera focal distance.

According to one embodiment, the present invention method further comprises a step 140 of estimating a lung volume as a function of time by multiplying the respiratory signal by the surface of the region of interest. The equation expressing the value of the lung volume V (k) as a function of time may be obtained from the following equation:

$$V(k) = D(k) \times S \tag{8}$$

wherein D (k) is the measure of average depth variation estimated for k-th image of the acquisition sample and S is a parameter representing the surface of the region of interest quantified in $mm^2$. The application of this equation allows to obtain from the depth images a curve of the lung volume as a function of time V (k), which presents a peak for each inhalation and a valley for each exhalation of the subject.

According to the embodiment wherein the ROI is automatically defined, the parameter S is calculated as the surface of the calculated region of interest, quantified in $mm^2$.

According to one embodiment, the lung volume as a function of time may be calculated as follows $$V(k) = D(k) \times S \times 10^3$$

where the multiplicative factor $10^3$ allows the convention from a volume in $mm^3$ to a volume quantified in ml.

According to one embodiment, the present invention method further comprises a step of estimating the tidal volume as the difference amplitude between the maximum value and the minimum value in one respiratory cycle of the respiratory signal multiplied by the surface of the region of interest, i.e. the difference amplitude between the maximum value and the minimum value in one respiratory cycle of the lung volume V(k). The estimation of this tidal volume is a key parameter for the monitoring of ventilated patient.

In one embodiment, the peaks in the curve of the lung volume as a function of time V(k) are detected in a given time window comprising at least one respiratory cycle, for example of the order of the minute. An algorithm of peak detection, known by the person skilled in the art, may be used to implement this step. The amplitude between the maximum value and the minimum value of each peak corresponds to the volume inhaled by the subject in the corresponding respiratory cycle. In this embodiment, the tidal volume is calculated as the average value of the amplitudes, calculated for multiple respiratory cycles, in the given time window. The tidal volume may be expressed as average value obtained from each respiratory cycle, advantageously allowing to avoid errors caused by random noise as well as irregularities and variability of the acquired measures. This value is crucial to assess breathing, offering the opportunity for early intervention, adjustment of the ventilation parameters or diagnosis of abnormalities.

According to one embodiment, the method also comprises estimating a minute volume, which represents the volume per minute calculated as the product of the respiratory rate and the tidal volume obtained for the ROI comprising the whole torso.

According to one embodiment, the method further comprises a step of controlling a ventilator by modifying the value at least one ventilation parameter, wherein the value of said ventilation parameter is calculated using at least one of the estimated respiratory parameters, notably the tidal volume. For example, the ventilation parameters to be controlled may be the volume or the pressure delivered by the ventilator to a patient under mechanical ventilation. This embodiment advantageously allows to adapt the respiratory therapy delivered by the ventilator to each patient, notably to his/her anatomy and current state of health.

According to one embodiment, the method further comprises a step of detecting the presence of respiratory abnormalities such as pneumothorax, atelectasis, diaphragmatic paradox etc. by monitoring multiple regions of interest on the torso of the patient, according to the embodiments described hereabove.

Figure 3:
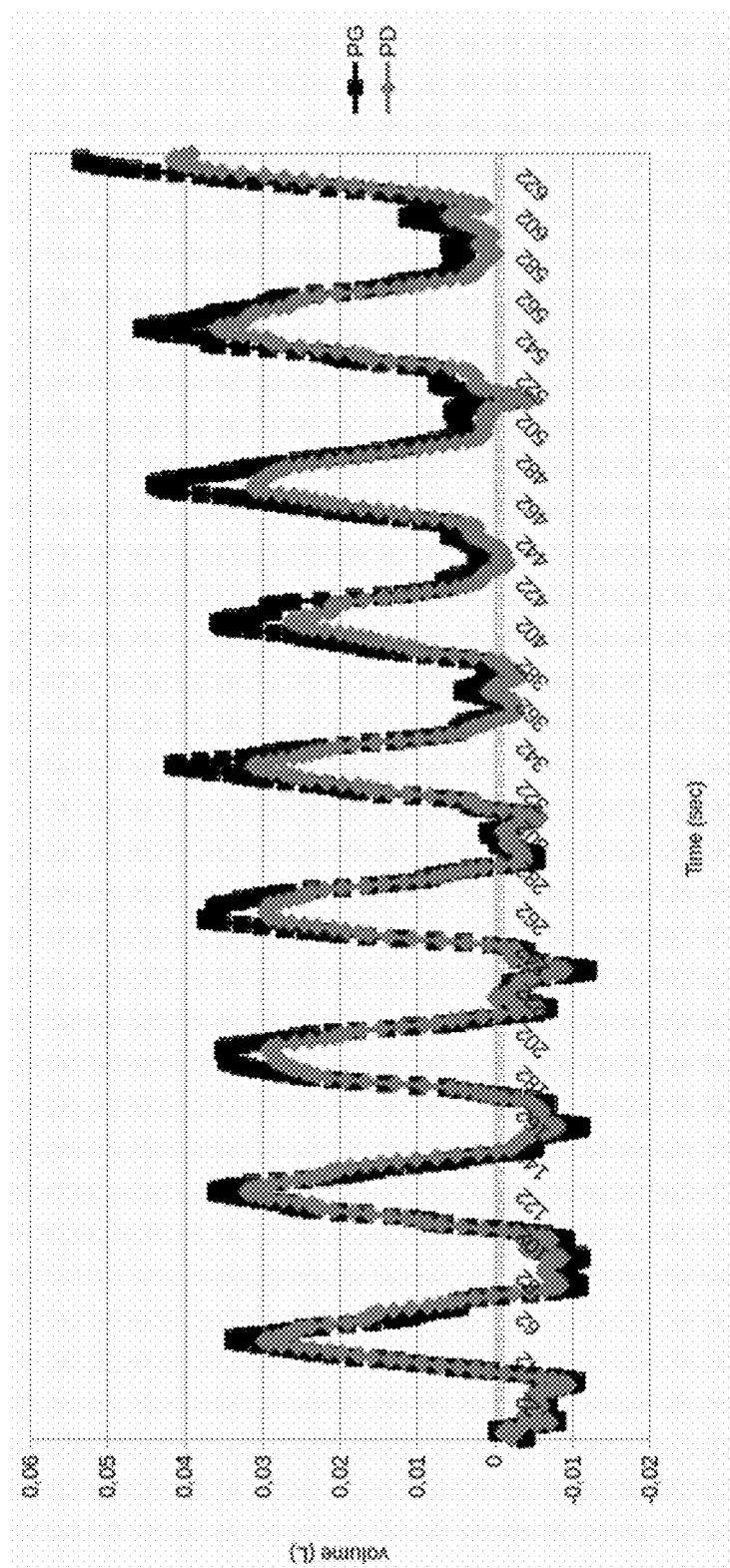
FIG. 3 is a graph representing the lung volume as a function of time in the left lung (black landmark) and in the right lung (grey landmark) of a subject.

As described above, the region of interest may be defined manually or automatically. In one embodiment, the ROI is automatically defined on one half of the thorax so as to cover only the surface of one lung. In this embodiment, a first region of interest is defined on the right lung and a second region of interest is defined on the left lung of the patient. The respiratory rate and the tidal volume are calculated, according to the embodiments hereabove, in the first region of interest and in the second region of interest. The monitoring of the respiratory rate and the tidal volume on the first and second ROI corresponds to the monitoring of these parameters separately in the left and right lung. It is as well possible to estimate a minute volume, which represents the volume per minute calculated as the product of the respiratory rate and the tidal volume in the first and second region of interest. FIG. 3 shows an example, for a patient, of lung volume calculated in the left lung (black line and landmarks) overlapped to the lung volume calculated in the right lung (gray line and landmarks). In this example, the evolution as a function of time of the lung volume in the left and right lung is homogeneous. The comparison of the respiratory rate and the tidal volume on the first and second ROI advantageously allows to evaluate the distribution of the lung volume between the two lungs and detects lungs heterogeneity. This information advantageously allows to detect uneven air volume distribution and depict regional abnormalities so as to diagnose respiratory problems such as pneumonitis or pneumonia and lead to an optimal ventilation adjusted according to the patient needs.

In one embodiment, the ROI detection and tracking step is configured to take into account all changes in the thorax surface happened during the acquisition.

Figure 4:
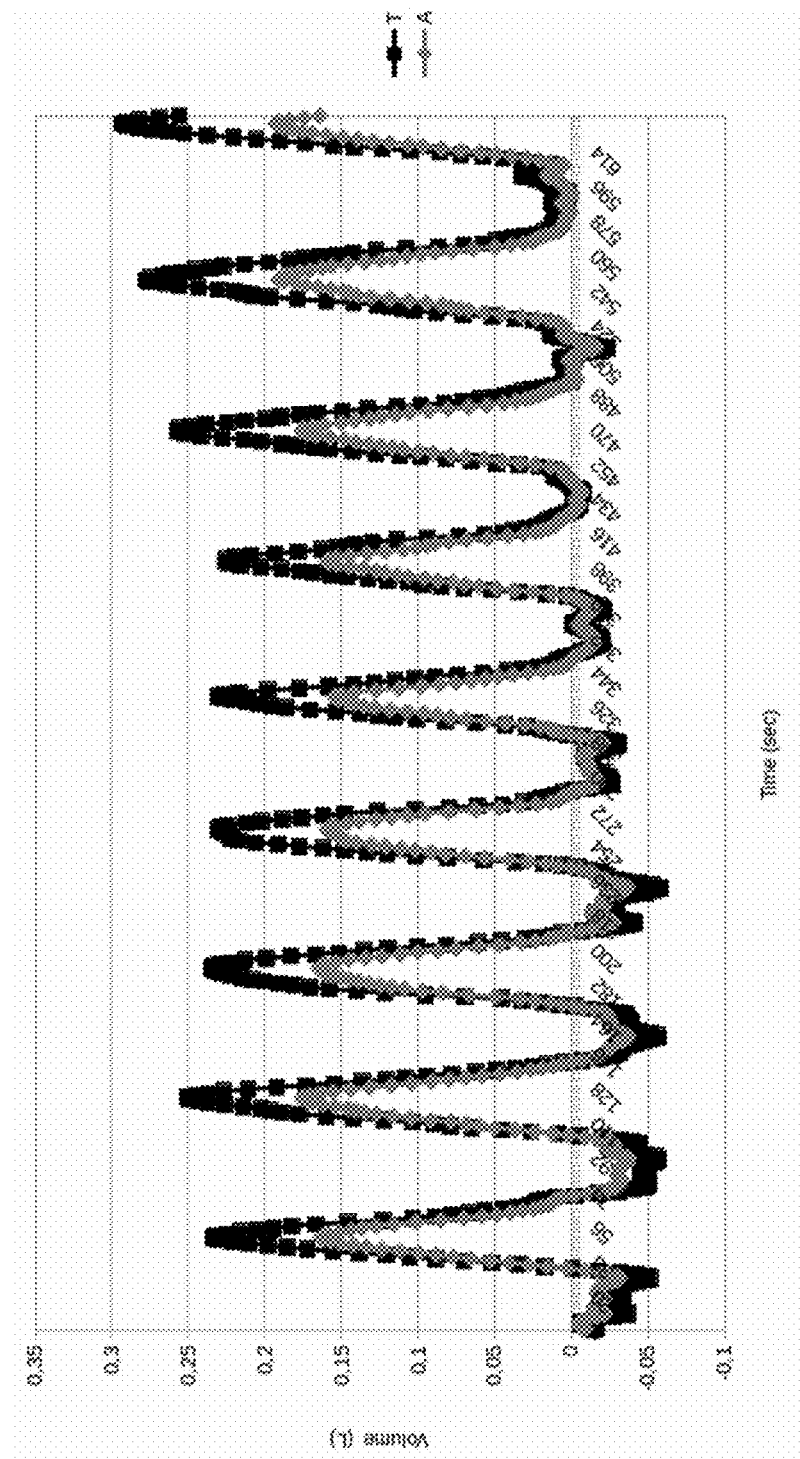
FIG. 4 is a graph representing the lung volume as a function of time in the thoracic region (black landmark) and in the abdominal region (grey landmark) of a subject.

In one alternative embodiment, the thoracic region and on the abdominal region are defined as region of interest. The respiratory rate and the tidal volume are calculated, according to the embodiments hereabove, in the thoracic region and in the abdominal region so as to monitor these parameters separately in the thorax and in the abdomen. The monitoring of respiratory parameters the abdominal and thoracic regions advantageously allows to detect paradoxical breathing (also called thoracoabdominal paradox) where the lungs and diaphragm moves in the opposite directions of their normal movements. This information notably allows to diagnose physiologic disturbances such as respiratory distress, trauma, neurological problems, and the like. FIG. 4 shows an example for a patient, of lung volume calculated in the thoracic region (black line and landmarks) overlapped to the lung volume calculated in the abdominal region (gray line and landmarks). In this example, the evolution as a function of time of the lung volume in the thorax and abdomen is correlated.

According to one embodiment, the method further comprises a step 150 of analyzing a respiratory signal of the patient in order to calculate a respiratory rate from the morphologic changes on the surface image of the torso.

According to one embodiment, the respiratory rate is calculated from the detection of inspiration peaks in a respiratory signal. The peaks detection may be performed using a technique for extrema detection using an amplitude threshold. This technique consists in the detection of maxima and minima in the respiratory signal by searching for signs changes on the ensemble of the acquisition sample. The acquisition sample may correspond to an acquisition interval of 10 seconds to 5 minutes. In one example considering an acquisition sample in an acquisition interval of 1 minute, it may be considered that the relative extrema (maximum and minimum) are superior in absolute value of the average value of the respiratory signal in the acquisition interval. Once the peaks detected, the respiratory rate is determined on the basis of the number of peaks in the acquisition interval.

In one example, the clinical data were acquired on patients admitted to the medical Intensive Care Unit at the CHU Cavale de Brest. The monitoring was carried out over a period of 10 to 20 minutes. Thus, for each patient, the ventilation parameters were calculated for each minute of acquisition (from 10 to 20 measurements per patient).

The method 100 for measuring respiratory parameters has been validated on 35 patients (30 of whom are intubated and 5 are spontaneously ventilated). For the 30 intubated patients, the results were compared with the clinical system measurements (respirator) and an average difference of 30±19 mL was found for the calculation of tidal volume. As for the respiratory rate, the average difference is 1.8±1.4 cpm. These values are well below the clinically acceptable limit.

Regional volume monitoring (right and left lung) was tested on a phantom connected to a respirator. The phantom has an asymmetrical operating mode that allows the air to be insufflated only in the right lung (one valve is open and the other remains closed). The calculated volume was compared with that set and 90% of the theoretical volume insufflated was detected in the right lung.

Figure 5:
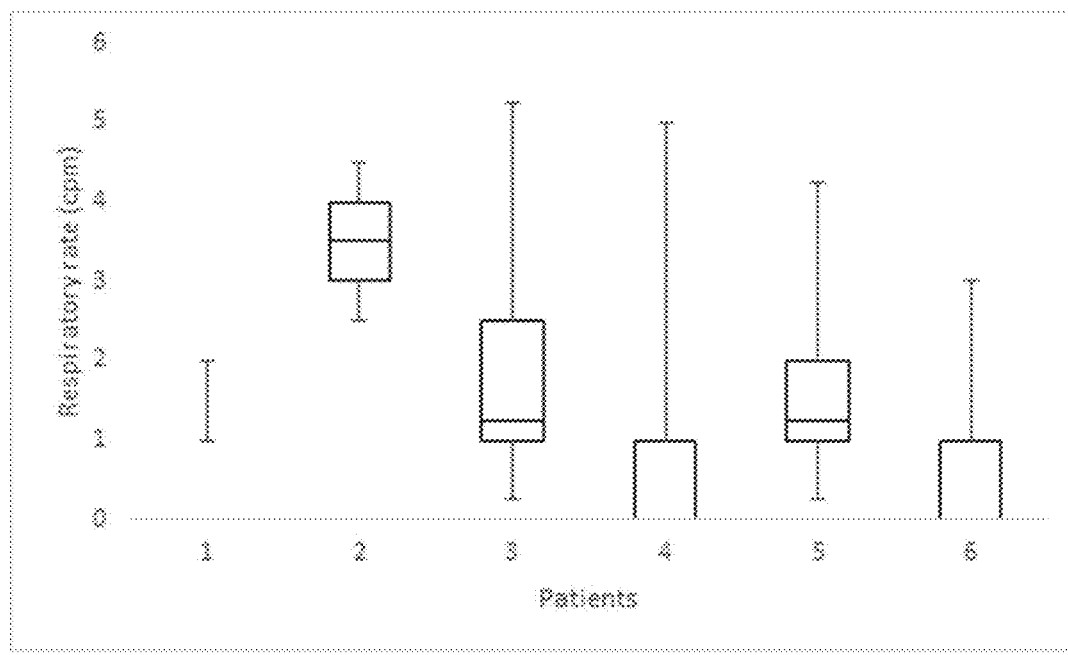
FIG. 5 is a box plot representing the median value, one standard deviation above and below the mean of the data, the minimum and the maximum of the respiratory rate parameter calculated for six patients.
Figure 6:
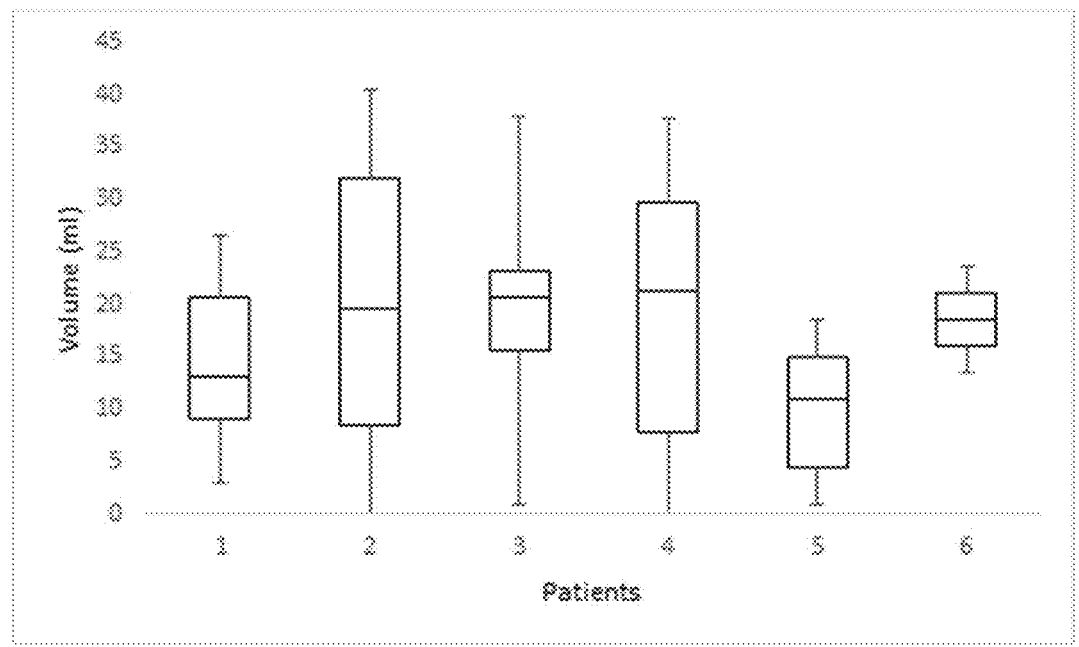
FIG. 6 is a box plot representing the median value, one standard deviation above and below the mean of the data, the minimum and the maximum of the tidal volume parameter calculated for six patients.

FIGS. 5 and 6 show boxplot graphs for the respiratory rate and tidal volume in 6 patients. The average error obtained on the measurements of these patients is 20±9 mL for calculating the tidal volume and 1.6±1.1 cpm for calculating the respiratory rate.

The present invention further relates to a program comprising instructions which, when the program is executed by a computer, cause the computer to carry out the steps of the method according to any one of embodiments described hereabove.

The computer program product to perform the method as described above may be written as computer programs, code segments, instructions or any combination thereof, for individually or collectively instructing or configuring the processor or computer to operate as a machine or special-purpose computer to perform the operations performed by hardware components. In one example, the computer program product includes machine code that is directly executed by a processor or a computer, such as machine code produced by a compiler. In another example, the computer program product includes higher-level code that is executed by a processor or a computer using an interpreter. Programmers of ordinary skill in the art can readily write the instructions or software based on the block diagrams and the flow charts illustrated in the drawings and the corresponding descriptions in the specification, which disclose algorithms for performing the operations of the method as described above.

The present invention further relates to a non-transitory computer readable medium comprising instructions which, when the program is executed by a computer, cause the computer to carry out the steps of the method according to any one of embodiments described hereabove.

Computer programs implementing the method of the present embodiments can commonly be distributed to users on a distribution computer-readable storage medium such as, but not limited to, an SD card, an external storage device, a microchip, a flash memory device, a portable hard drive and software websites. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

Yet another aspect of the present invention concerns a system S for measuring respiratory parameters of a subject, notably a patient.

Figure 2:
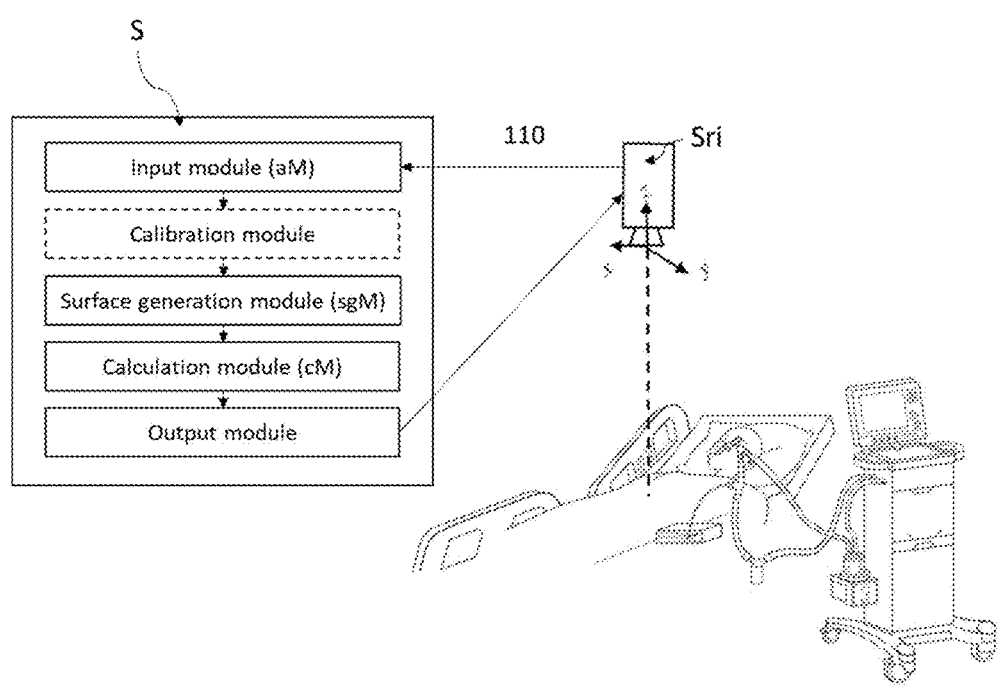
FIG. 2 is a schematic representation of the system of the invention according to one embodiment.

As shown in FIG. 2, the system of the invention comprises several modules configured to cooperate between each other's and carry out the steps of the method of the present invention.

According to one embodiment, the system comprises an input module aM configured to receive a set of acquisitions derived from a range imaging sensor Sri, said set of acquisitions comprising at least one raw image comprising at least one portion of a torso of the subject, wherein each point of the raw image represents the distance between the range imaging sensor Sri and the subject.

According to one embodiment, the system comprises an acquisition module aM configured to control a range imaging sensor Sri for the acquisition of at least one raw image comprising at least one portion of the torso of the patient, wherein each point of the raw image represents the distance between the range imaging sensor Sri and the patient.

The system may comprise a communication module that, through physical connection or wireless connection between the range imaging sensor Sri and the system for the transmission of acquisition instructions, controls the image acquisition and the reception of the acquired raw images.

According to one embodiment, the system comprises range imaging sensor Sri. The processor implementing the surface generation module and/or the calculation module may be connected to the range imaging sensor via usb3 bus.

In one preferred embodiment, the range imaging sensor Sri is a time-of-flight camera. The ToF camera may be a pulsed-light camera using pulsed-light sensor or a continuous-wave modulated-light camera using continuous-wave modulation sensor. The ToF cameras may combine a single or multiple laser beams, possibly mounted onto a rotating mechanism, with a 2D array of light detectors and time-to-digital converters, to produce 1-D or 2-D arrays of depth values. The ToF camera may implement laser diodes or a LED of different wavelengths, notably infrared or near infrared.

According to one embodiment, the time-of-flight camera uses infrared light illumination Several ToF cameras are actually available such as CamCube PMD from Photonic Mixer Devices (PMD) Technologies, SwissRanger 4000 or the sensor Kinect V1 of Microsoft. According to one embodiment, the ToF camera is a Kinect v2 RGB-D camera which uses multiple modulation frequencies (10-130 MHz) thus achieving an excellent compromise between depth accuracy and phase unwrapping.

As explained above, in a preferred embodiment, the range imaging sensor Sri is place in front of the thorax of the patient, notably fixe on the ceiling above him. This arrangement of the range imaging sensor Sri makes it possible to avoid introducing extra objects into the environment surrounding the patient. This is advantageous since an environment free from obstacles allows an easier access to the health staff in case of intervention on the patient.

According to one embodiment, the system comprises a calibration module configured to apply a rotation matrix to the raw images so as to align the patient thorax in the raw images with the xy plane of the time-of-flight camera. The calibration module is notably configured to implement the steps of the method of the present invention concerning the calibration step described in the embodiment hereabove.

According to one embodiment, the system comprises a surface generation module sgM.

According to one embodiment, the surface generation module sgM is configured perform a preliminary operation on the raw image consisting in filtering the raw image so as to remove noise originating from other objects in the scene.

According to one embodiment, the surface generation module sgM is configured to generate a surface image of at least one portion of the surface of the torso of the patient by surface interpolation of the raw image. The surface image may be obtained by said module using basis spline functions. The surface generation module sgM is notably configured to implement the steps of the method of the present invention concerning the step 120 of surface image generation described in the embodiment hereabove.

According to one embodiment, the system comprises a calculation module cM configured to calculate from the morphologic changes on the surface image of the torso respiratory parameters such as the tidal volume and the respiratory rate. In this embodiment, the calculation module cM is configured to calculate a respiratory signal as a function of time as the spatial average, in a given region of interest defined on the torso of the subject, of the differences between the depth values of the surface image at a given time and the depth values of a reference surface image and to calculate a tidal volume as the maximum value in one respiratory cycle of the respiratory signal multiplied by the surface of the region of interest.

The calculation module cM is notably configured to implement the steps of the method of the present invention concerning the steps 130 and 140 for the estimation of the tidal volume described in the embodiments hereabove.

According to one embodiment, the calculation module cM is configured to further calculate the respiratory rate calculated from the detection of inspiration peaks in the respiratory signal. The calculation module cM is notably configured to implement computational operations to obtain the respiratory rate according to the method's embodiments concerning the step 150, described above in the present specifications.

According to one embodiment, the system comprises an output module configured to provide as output said respiratory parameters. Said output information may be represented as a visual or an auditory output representing the results such as the lung volume, respiratory rate and/or the tidal volume. Said output module may be a display or a microphone connected wirelessly or not to the system.

According to one embodiment, the system is a data processing system such as dedicated circuitry or a general-purpose computer device (i.e. a processor), configured for receiving the raw images and executing the operations described in the embodiments described above. Said computer device may comprise a processor and a computer program. The data processing system may include, for example, one or more servers, motherboards, processing nodes, personal computers (portable or not), personal digital assistants, smartphones, smartwatches, smartbands, cell or mobile phones, other mobile devices having at least a processor and a memory, and/or other device(s) providing one or more processors controlled at least in part by instructions.

According to one embodiment, the computer device comprises a network connection enabling remote implementation of the method according to the present invention.

In one example, the input (i.e. raw data) is delivered to a data processing unit such as an integrated processor, wherein software and hardware are used to process the signal.

Output (respiratory features, alerts) are communicated to computing platform or user systems (computer, or tablet computer via wireless or wired network).

EXAMPLES

The present invention is further illustrated by the following examples.

Example 1—Patient Simulator Mannequin

Materials and Methods

A patient simulator mannequin, connected to a respirator that can deliver a volume from 100 to 500 ml at different respiratory rate (between 12 to 50). This mannequin has two operational modes: a symmetrical mode that allows the air to move into both lungs simultaneously and an asymmetric mode that allows air movements in only one lung (right lung). The first mode was used to evaluate the respiratory rate (RR) and tidal volume (Vt) in the mannequin torso and the second operation mode was used to evaluate the regional pulmonary function. A total of 21 mannequin's recordings over 10 minutes were analyzed and the respiratory measurements were calculated for each minute of acquisition. The estimated parameters were compared to the reference parameters (ventilator settings).

Results

Figure 7:
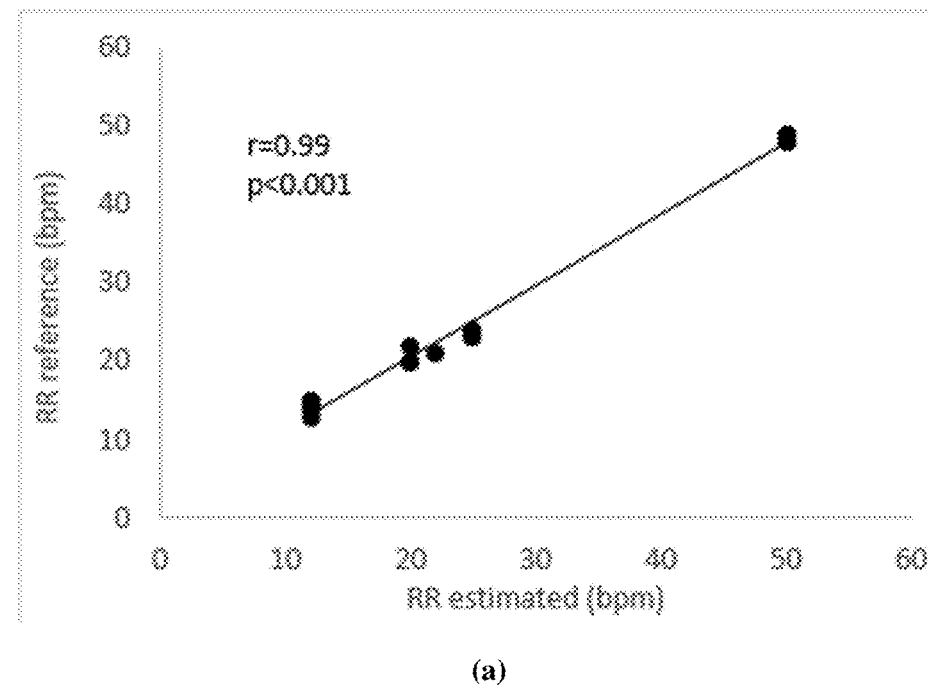
FIGS. 7(a) and (b) are a correlation and Bland-Altman plot for reference and estimated respiratory rates. Reference RR values are provided by the mannequin ventilator. Estimated RR was performed using the Kinect based monitoring system. On the 21 recordings, the estimation of the RR was highly correlated with the reference method (r=0.99; p<0.001). The comparison of the two methods using the Bland-Altman plot demonstrates low bias (0 bps) and deviation (<±1.86 bps).
Figure 7:
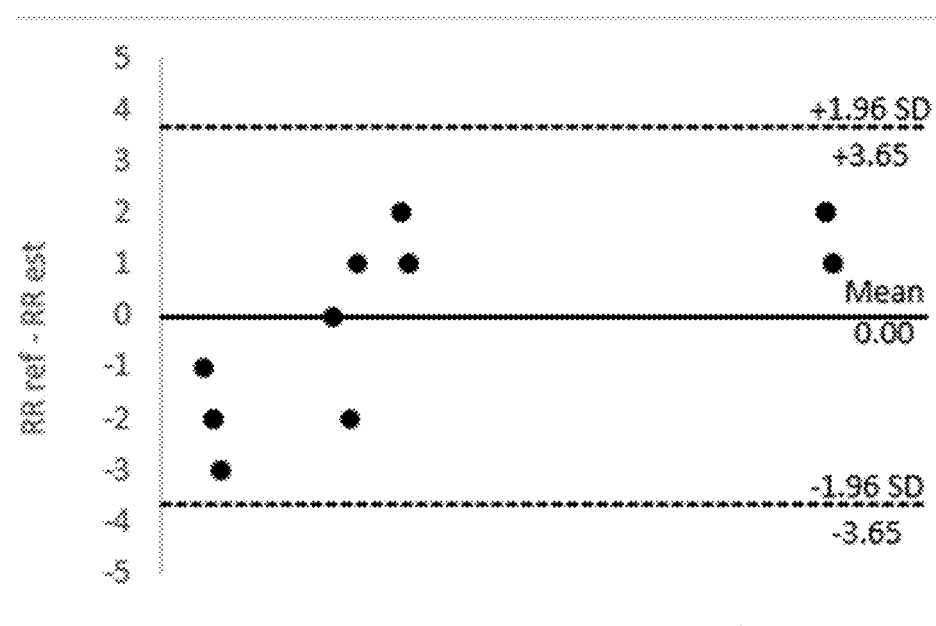

The results obtained by analyzing the mannequin recordings are reported in FIGS. 7(*a*) and (*b*). The scatter plot and regression line illustrate the degree of agreement between the reference and estimated RR. The correlation coefficient showed a high value (r=0.99; p<0.001) with a low bias (0 bps) and deviation (±1.86 bps). The mean error between reference and estimated RR show a value of 1.6±0.9 bps with a minimum of 0 bps and a maximum equal to 3 bps.

Figure 8:
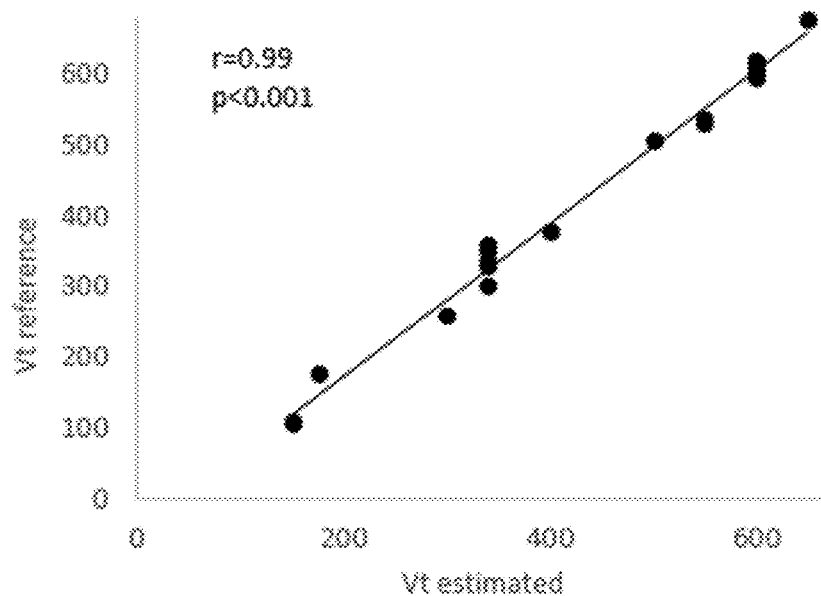
FIGS. 8(a) and (b) are a correlation and Bland-Altman plot for reference and estimated tidal volume. Reference Vt values are provided by the mannequin ventilator. Estimated Vt was performed using the Kinect based monitoring system. On the 21 recordings, the estimation of the RR was highly correlated with the reference method (r=0.99; p<0.001).
Figure 8:
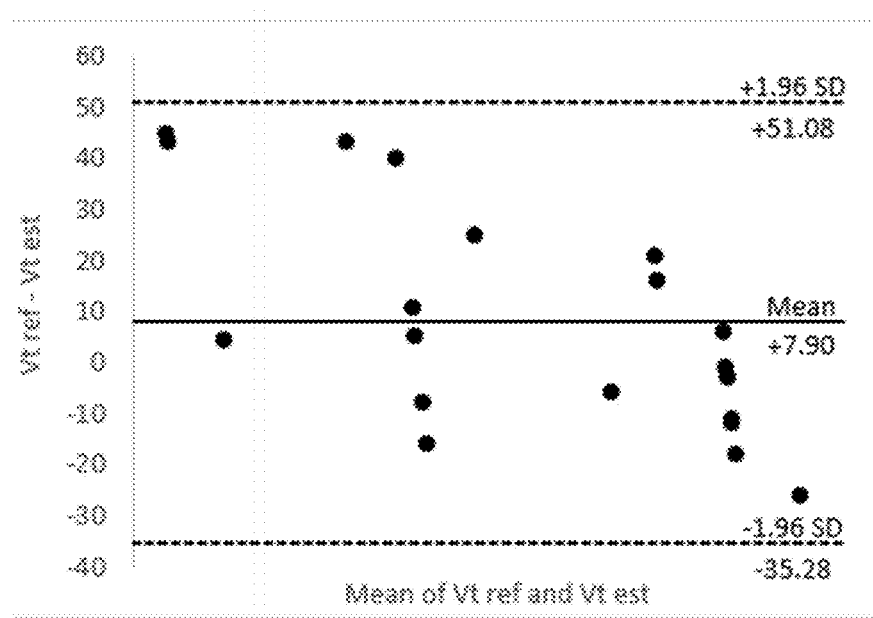

FIGS. 8(a) and (b) presents the correlation between the reference and estimated tidal volume. The scatter plot and linear regression demonstrate high agreement (r=0.99; p<0.001) with a low bias (7.90 ml) and acceptable deviation (±22.03 ml). The mean error is of value of 18.0±14.5 ml, with a minimum and maximum differences equal to 1 ml and 45 ml respectively.

The assessment of the regional volume using the mannequin's asynchronous mode allowing the air to pass only in the right lung, is presented in FIG. 9. The ventilator settings are set at 250 ml and 22 cpm.

The volume curves demonstrate that the air delivered by the ventilator is totally inhaled by the right lung. Although a slight fluctuation, due to the noise in depth measurements, appears in the left lung volume curve, this signal has extremely low amplitude and no evident patterns. The contribution of the right thorax to the total volume for all performed tests is 87.2%.

Example 2—Patients

Materials and Methods

This example relates to a clinical evaluation including 16 mechanically ventilated patients (10 males, 6 females) admitted in the ICU at the Brest University Hospital.

The procedure of invasive ventilation often involves the use of sedation and paralyzing agents, to ensure patient safety and optimize the air exchange. This helps prevent asynchrony with the ventilator and intolerance to the endotracheal tube. According to sedation or the consciousness levels, the patient spontaneous ventilation may not be maintained. The commonly used ventilation mode is the Assist-Control Ventilation (ACV), one patient had a Pressure Support Ventilation mode (PSV) assisting and supporting the patient's spontaneous breath. The ventilator settings were defined according to the patient physiology and pathology. Patients' physiological characteristics are summarized in Table 1.

TABLE 1

| General characteristics (n = 16) | |
|---|---|
| Age (mean = std) | 71 ± 7 |
| Sex ratio (F/M) | 6/10 |
| IMC (kg/m$^2$) | 26.5 ± 7.9 |
| Admission diagnosis | |
| Respiratory failure n-(%) | 4 (25.0%) |
| Cardiovascular failure n-(%) | 6 (37.5%) |
| Neurological failure n-(%) | 3 (18.7%) |
| other | 3 (18.7%) |
| IV sedation n-(%) | 7 (43.7%) |
| Paralyzing agents n-(%) | 1 (16.6%) |
| REEP (cm H2O; mean ± SD) | 6.2 ± 2.9 |
| ventilator mode n-(%) | |
| ACV | 15 (93.7%) |
| PSV | 1 (6.2%) |

During the evaluation phase, respiratory parameters calculations were automatically and continuously measured using the system. A total of 216 recordings were analyzed considering a monitoring period of 10 to 20 minutes for each patient. RR and Vt estimated parameters were compared to the reference values provided by the ventilator (considered as the gold standard). However, the reference of regional volume (Vr) parameter is not available as it cannot be measured by the ventilator. The comparison between the estimated parameters and the reference parameters is performed based on the Linear correlation using Pearson's analysis. Pearson's correlation coefficient is a statistical measure of the strength of a linear relationship between paired data. It requires variables to be normally distributed, continuous and have a linear relationship. Data normality was checked by using the D'Agostino and Pearson omnibus normality test.

Additionally, the mean error (mean absolute difference between the reference and estimated values±standard deviation (std)) was calculated to assess the accuracy and reliability of the present method.

Finally, to evaluate the pose estimation algorithm within the particular clinical ICU environment, the success/failure rate of the algorithm to detect the patient's thorax was measured. The standard way to measure the success/failure rate is to count the number successful/failed detection on the total number of runs.

Results

A total of 216 ICU patients' recordings were analyzed. The degree of agreement between the estimated and reference RR is reported in FIG. 10. The scatter plot and linear regression show high correlation (r=0.95; p<0.0001) with a low bias (0.39 bps) and deviation (±1.7 bps).

Figure 11:
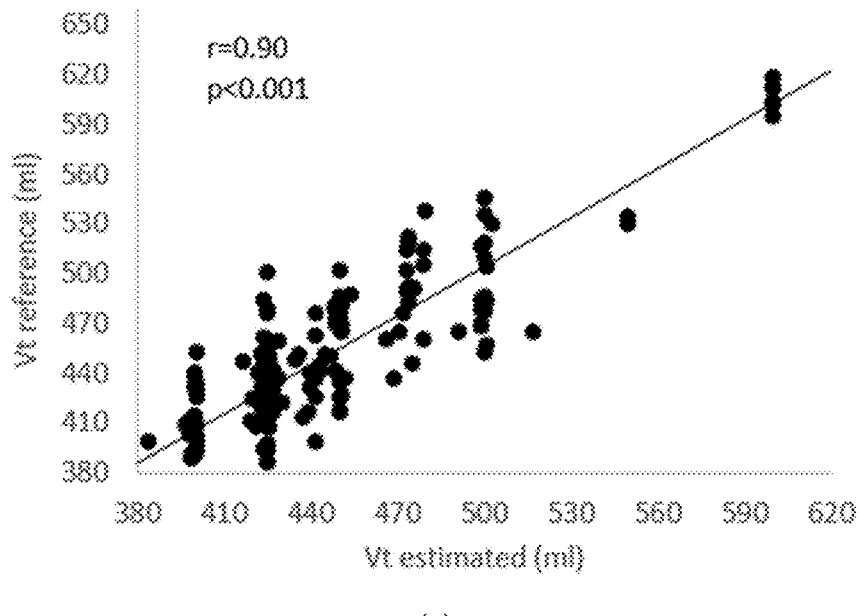
Figure 11:
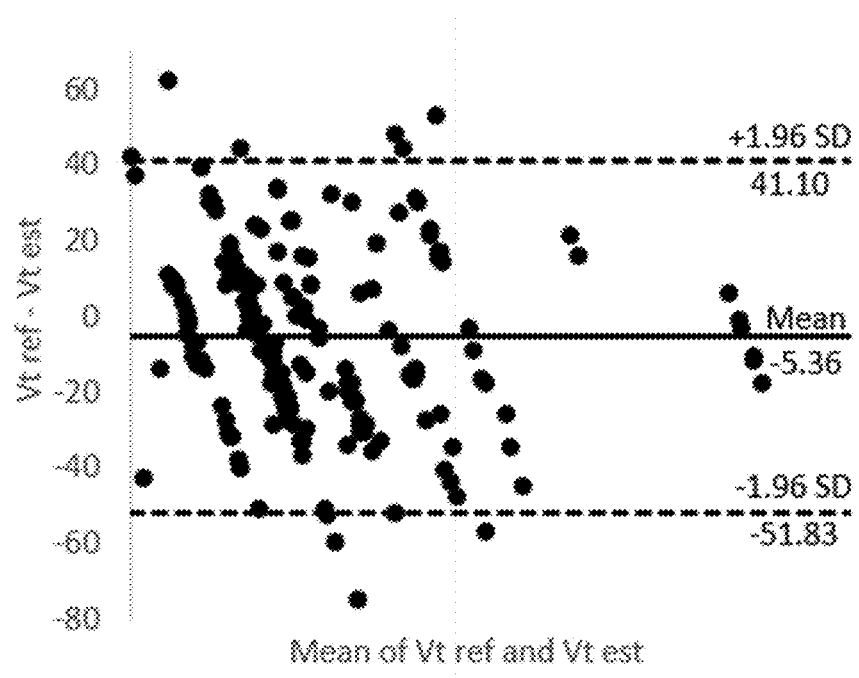

The results of RR estimation show that 84.7% have an error less than or equal to 2 bps. Only 4.1% of the measurements have an error greater than 3 bps. The minimum and maximum deviations are equal to 0 and 5 bps respectively. The mean error calculated on the total patients' recordings shows a value of 1.3±1.1 bps. The Vt estimation in patient population, presented in FIG. 11, illustrate a strong correlation with the reference values (r=0.90; p<0.0001) with a low bias (−5.3 ml) and deviation (<±23.7 ml).

These results show that 69.0% of the estimated Vt is less than 25 ml. Only 6.4% of the measurements were greater than 35 ml. The mean error calculated on the total patients' recordings is 19.6±14.2 ml.

To evaluate the measurements variability, FIG. 12 and FIG. 13 report the mean error (mean difference±standard deviation) calculated on the recordings of each patient separately.

FIG. 12 shows that the mean error of RR estimation of each patient is less than 3 bps. The minimum and maximum standard deviations are equal to 0.4 and 1.49 bps respectively. The smallest error and standard deviation is observed in patient 1's recordings (1.1±0.4 bps).

The Vt estimation of each patient, illustrated in FIG. 13, shows an error less than 28 ml for each patient. The minimum and maximum standard deviation are equal to 5.0 and 18.2 ml respectively. The smallest error and standard deviation (8.5±6.3 ml) is observed in patient 1's recordings while the greater error and standard deviation (26.7±17.2 ml) is observed in the recordings of patient 11.

Figure 14:
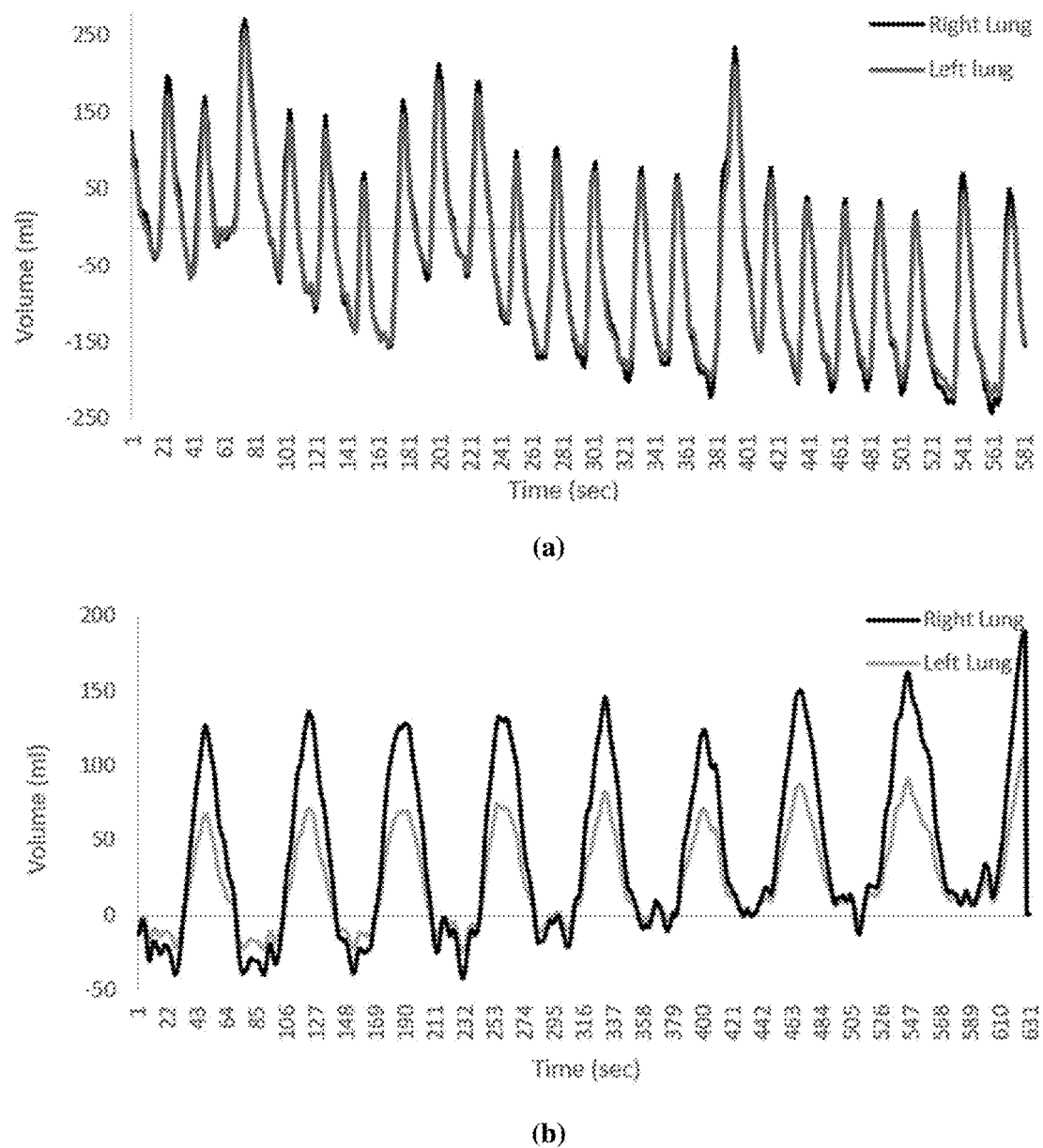

Further results on regional monitoring are presented in the figures below. However, quantitative analysis could not be performed because of the absence of the ground truth due to the lack of clinical noninvasive devices for regional monitoring. An example of the regional monitoring in the left and right lungs of two ICU patients is illustrated in FIG. 14. The volume time curves in FIG. 14(a) in the left lung (black curve) and the right lung (gray curve) revealed a good match of volume distribution while FIG. 14(b) demonstrates unequal volume distribution between the left and right.

Figure 15:
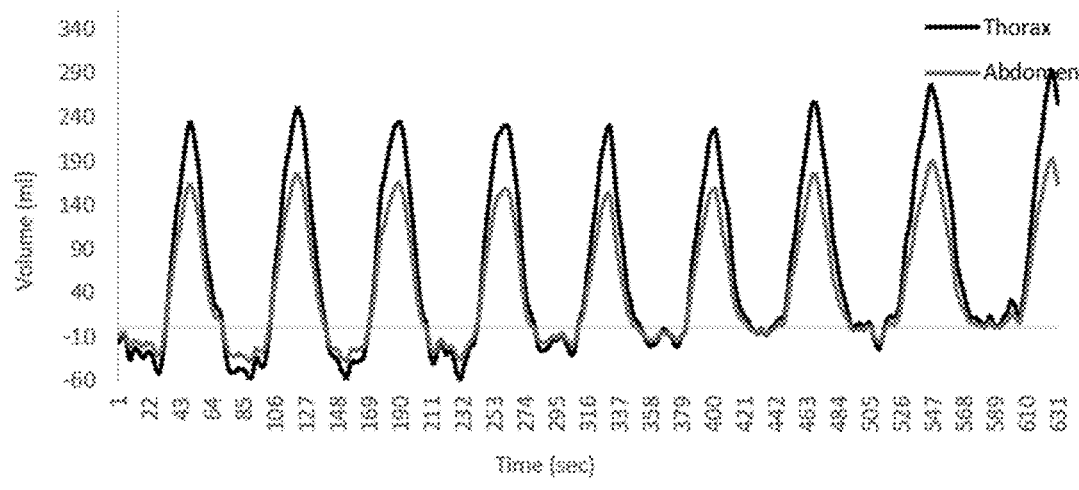
Figure 15:
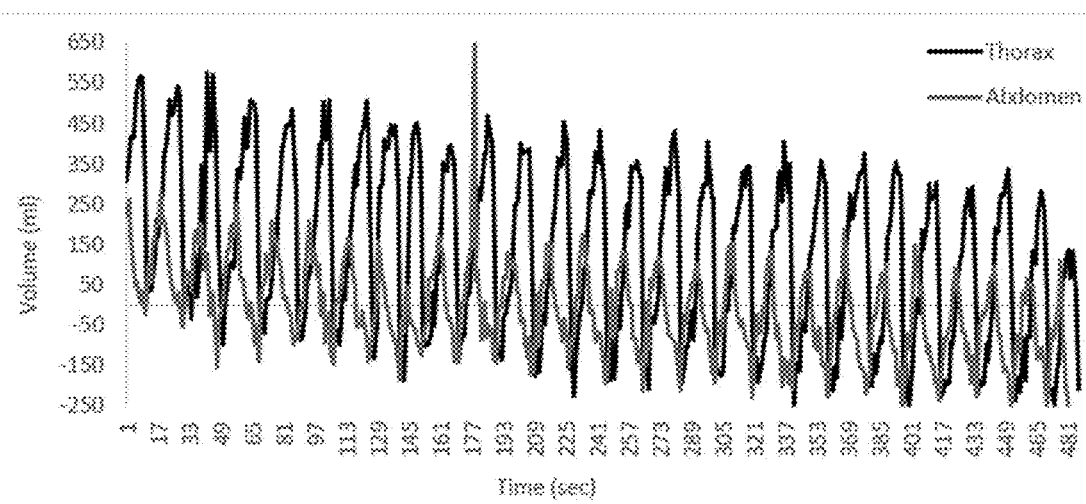

Another example presented in FIG. 15, illustrates the regional monitoring in the thoracic and abdominal region of two ICU patients. In FIG. 15(a) the volume time curves are synchronized while FIG. 15(b) shows asynchronous movements between the rib cage and the abdomen.

The invention claimed is:

1. A computer-implemented method for estimating respiratory parameters of a subject, wherein said method comprises:
    receiving a set of acquisitions derived from a range imaging sensor, said set of acquisitions comprising at least one raw image and a reference surface image of at least one portion of a torso of the subject, wherein each point of said at least one raw image represents a distance between the range imaging sensor and the subject; said reference surface image comprising depth values;
    generating, for each raw image of said at least one raw image, a surface image of at least one portion of a surface of the torso of the subject by surface interpolation of said at least one raw image;
    estimating a respiratory signal as a function of time by;
        for each surface image, calculating the differences between depth values comprised in a given region of interest (ROI) defined on the surface image, said region of interest (ROI) comprising at least portion of the torso of the subject, at a given time, and the depth values of said reference surface image, and
        calculating the spatial average of the obtained differences;
    estimating respiratory parameters including at least a lung volume as a function of time by multiplying the respiratory signal by a surface of the region of interest; and
    providing as output said respiratory parameters.

2. The method according to claim 1, further comprising estimating a tidal volume as the difference between the maximum value and the minimum value in one respiratory cycle of the respiratory signal multiplied by the surface of the region of interest.

3. The method according to claim 1, further comprising estimating a respiratory rate calculated from the detection of inhalation peaks in the respiratory signal.

4. The method according to claim 1, wherein surface interpolation of said at least one raw image is obtained using basis spline functions.

5. The method according to claim 1, further comprising filtering said at least one raw image so as to remove noise originating from other objects in a scene.

6. The method according to claim 1, wherein said at least one raw image is derived from the range imaging sensor being a time-of-flight camera.

7. The method according to claim 6, wherein the method further comprises calibrating by applying a rotation matrix to said at least one raw image so as to align the subject torso in said at least one raw image with a xy plane of the time-of-flight camera.

8. The method according to claim 1, wherein said at least one raw image is derived from the range imaging sensor being placed in front of the torso of the subject.

9. A non-transitory computer readable medium comprising instructions which, when the program is executed by a computer, cause the computer to carry out the method according to claim 1.

10. A system for estimating respiratory parameters of a subject comprising:
    at least one input selected from the group consisting of hardware, software, firmware and combinations thereof, said at least one input being configured to receive a set of acquisitions derived from a range imaging sensor, said set of acquisitions comprising at least one raw image and a reference image of at least one portion of a torso of the subject, wherein each point of the at least one raw image represents a distance between the range imaging sensor and the subject, said reference surface image comprising depth values;
    at least one processor configured to:
        generate, for each raw image of said at least one raw image, a surface image of at least one portion of a surface of the torso of the subject by surface interpolation of said at least one raw image,
        estimate a respiratory signal as a function of time by:
            for each surface image, calculating the differences between depth values comprised in a given region of interest (ROI) defined on the surface image, said region of interest (ROI) comprising at least portion of the torso of the subject, at a given time, and the depth values of said reference surface image, and
            calculating the spatial average of the obtained differences,
        calculate respiratory parameters including at least a lung volume as a function of time by multiplying the respiratory signal by the surface of the region of interest; and
    at least one output selected from the group consisting of hardware, software, firmware and combinations thereof, said at least one output being configured to output said respiratory parameters.

11. The system according to claim 10, wherein the at least one processor is configured to further calculate a respiratory rate calculated from the detection of inhalation peaks in the respiratory signal.

12. The system according to claim 11, wherein the range imaging sensor is placed in front of the torso of the subject.

13. The system according to claim 10, wherein the range imaging sensor is a time-of-flight camera and the at least one processor is further configured to apply a rotation matrix to said at least one raw image so as to align the subject torso in said at least one raw image with the xy plane of the range imaging sensor.

14. The system according to claim 10, wherein the at least one processor is further configured to calculate a tidal volume as the difference between the maximum value and the minimum value in one respiratory cycle of the respiratory signal multiplied by the surface of the region of interest.

15. The system according to claim 10, wherein the at least one processor is further configured to filter said at least one raw image so as to remove noise originating from other objects in a scene.

16. The system according to claim 10, wherein surface interpolation of said at least one raw image is obtained using basis spline functions.

* * * * *